(12) United States Patent
Narula et al.

(10) Patent No.: US 7,390,772 B2
(45) Date of Patent: ***Jun. 24, 2008

(54) 1-PHENYL-SPIRO[2.5]OCTANE-1-CARBONITRILE ANALOGUES THEIR USE IN FRAGRANCE FORMULATIONS

(75) Inventors: Anubhav P. S. Narula, Hazlet, NJ (US); Edward Mark Arruda, Cliffwood, NJ (US); Patrick M. Merritt, Trenton, NJ (US); Franc T. Schiet, Naarden (NL)

(73) Assignee: International Flavor & Fragrances Inc., New York, NY (US)

( * ) Notice: Subject to any disclaimer, the term of this patent is extended or adjusted under 35 U.S.C. 154(b) by 72 days.

This patent is subject to a terminal disclaimer.

(21) Appl. No.: 11/419,081

(22) Filed: May 18, 2006

(65) Prior Publication Data

US 2007/0270328 A1    Nov. 22, 2007

(51) Int. Cl.
*C11D 3/50*    (2006.01)
(52) U.S. Cl. .............................. 510/102; 558/388; 512/8
(58) Field of Classification Search ............... 510/102; 512/8; 558/388
See application file for complete search history.

(56) References Cited

U.S. PATENT DOCUMENTS

| 4,399,076 | A |   | 8/1983  | Fayter, Jr. et al. |         |
|-----------|---|---|---------|--------------------|---------|
| 5,994,376 | A | * | 11/1999 | Freyne et al.      | 514/341 |
| 6,063,956 | A |   | 5/2000  | Ross et al.        |         |
| 6,069,125 | A |   | 5/2000  | Pesaro             |         |
| 6,777,409 | B2| * | 8/2004  | Jaroch et al.      | 514/230.5 |

FOREIGN PATENT DOCUMENTS

| EP | 1024135 | 8/2000 |
| WO | WO9933786 | 7/1999 |

OTHER PUBLICATIONS

Tsutomu Kumagai et al.: "Photoreaction of Alpha-phenylcrotonitrile Derivatives: The Facil Cyclopropane Ring Formation" Tetrahedron Letters., 27(51), 1986, pp. 6225-6228.
J. Ranfaing et al.: "Stereochimie de la Cyclisation Du Dibromo-1,3 Butane et du Dibromo-1,2 Propane sur les Sels Metalliques du Phenylacetonitrile" Tetrahedron Letters., 15, 1974, pp. 1439-1442.
European Search Report.

* cited by examiner

*Primary Examiner*—John R. Hardee
(74) *Attorney, Agent, or Firm*—Elizabeth M. Quirk; XuFan Tseng; Joseph F. Leightner

(57) ABSTRACT

The present invention is directed to novel compounds of the general formula

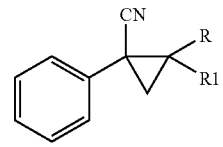

wherein R and $R^1$ independently represent a hydrogen or a straight, branched or cyclic hydrocarbon moiety consisting of less than 15, preferably less than 10, most preferably less than 4 carbon atoms and containing single and/or double bonds.

Another embodiment of the invention is a method for enhancing a perfume composition by incorporating an olfactory acceptable amount of the compound provided above.

18 Claims, No Drawings

1-PHENYL-SPIRO[2.5]OCTANE-1-CARBONITRILE ANALOGUES THEIR USE IN FRAGRANCE FORMULATIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel compounds, represented by Formula I set forth below:

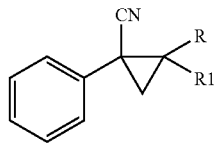

Formula I wherein R and $R^1$ independently represent a hydrogen or a straight, branched or cyclic hydrocarbon moiety consisting of less than 15, preferably less than 10, most preferably less than 4 carbon atoms and containing single and/or double bonds, and wherein R and R1 taken together can form a cyclic hydrocarbon moiety consisting of less than 10, more preferably less than 7 and most preferably less than 6 carbon atoms.

Another embodiment of the invention is a method for enhancing a perfume composition by incorporating an olfactory acceptable amount of the compound provided above.

These and other embodiments of the present invention will be apparent by reading the following specification.

DETAILED DESCRIPTION OF THE INVENTION

In Formula I above, R and $R^1$ independently represent a hydrogen or a straight, branched or cyclic hydrocarbon moiety consisting of less than 15, preferably less than 10, most preferably less than 4 carbon atoms and containing single and/or double bonds, and wherein R and R1 taken together can form a cyclic hydrocarbon moiety consisting of less than 10, more preferably than 7 and most preferably less than 6 carbon atoms. Suitable straight hydrocarbon moieties include ethyl, propyl, butyl, pentyl, hexyl, and the like. Suitable branched hydrocarbon moieties include isopropyl, sec-butyl, tert-butyl, diethyl, 2-ethyl-propyl, and the like. Suitable cyclic hydrocarbon moieties include cyclopropyl, cyclobutyl, cyclopentyl, cyclohexyl, phenyl, and the like. Suitable hydrocarbon moieties containing double bonds include ethene, propene, 1-butene, 2-butene, penta-1-3-deine, hepta-1,3,5-triene and the like.

In the most preferred embodiment of the invention, the novel compounds of the present invention are represented by the following structures:

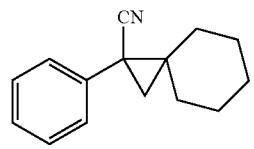

Formula II

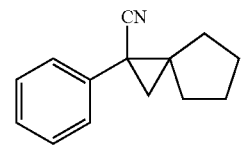

Formula III

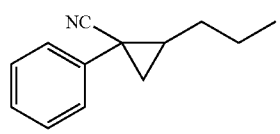

Formula IV

Those with the skill in the art will appreciate that the compound of Formula II is 1-Phenyl-Spiro[2.5]Octane-1-Carbonitrile, the compound of Formula III is 1-Phenyl-Spiro[2.5]heptane-1-Carbonitrile and the compound of Formula IV is 1-Phenyl-2-Propyl-cyclopropanecarbonitrile.

The table below lists additional compounds derived from Formula I that are described in the present invention:

| R | $R^1$ | Compound |
|---|---|---|
| H | H | 1-phenyl-cyclopropanecarbonitrile |
| $CH_3$ | H | 2-methyl-1-phenyl-cyclopropanecarbonitrile |
| $CH_3$ | $CH_3$ | 2,2-dimethyl-1-phenyl-cyclopropanecarbonitrile |
| $CHCH_2CH_3$ | H | 1-phenyl-2-propenyl-cyclopropanecarbonitrile |
| $CH(CH_3)_2$ | H | 2-isopropyl-1-phenyl-cyclopropanecarbonitrile |

-continued

| R | R¹ | Compound |
|---|---|---|
| CH₃ | (cyclohexyl) | 2-cyclohexyl-2-methyl-1-phenyl-cyclopropanecarbonitrile |
| CH₃ | (cyclopentyl) | 2-cyclopentyl-2-methyl-1-phenyl-cyclopropanecarbonitrile |
| CH₃ | (cyclopentadienyl) | 2-cyclopenta-2,4-dienyl-2-methyl-1-phenyl-cyclopropanecarbonitrile |
| CH₂CH₂CH₃ | CH₂CH₂CH₃ | 1-phenyl-2,2-dipropyl-cyclopropanecarboxaldehyde |
| (CH)₄CH₂CH₃ | H | 2-hexa-1,3-dienyl-1-phenyl-cyclopropanecarbonitrile |

The compounds of the present invention may be prepared from the corresponding alkenes via a Corey's cyclopropanation reaction of the following sequence:

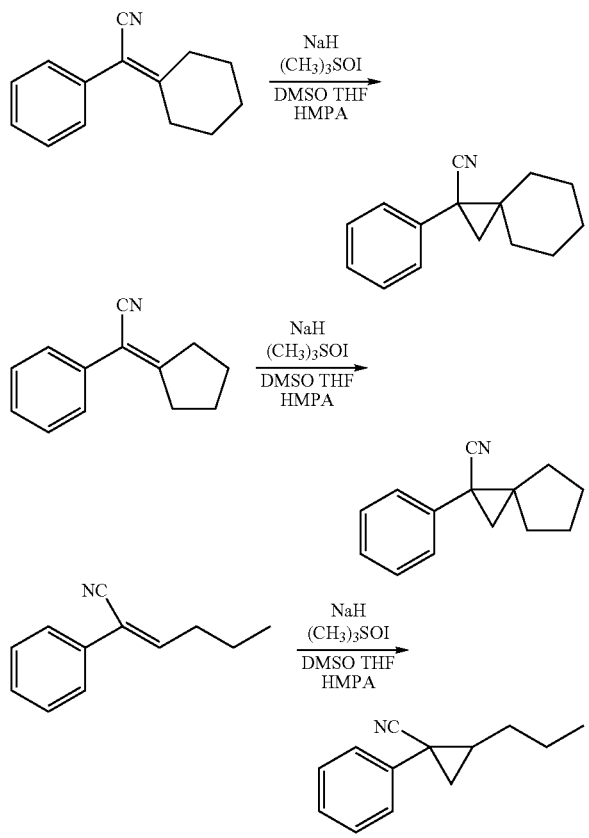

The starting materials for the above reactions are commercially available from Aldrich.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as HPLC, and particularly gel chromatography and solid phase microextraction ("SPME").

We have discovered that the fragrance compounds of Formulae II-IV have fresh, floral, ionone, soft, substantive, citrus and green tones and are well suited for use as a fragrance ingredients.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc., New York, N.Y., USA.

EXAMPLE A

Preparation of
1-Phenyl-Spiro[2.5]Octane-1-Carbonitrile

To a dry 2 L multi-neck round bottom flask fitted with an air stirrer, nitrogen inlet condenser and an addition funnel 200 ml of Dimethyl Sufoxide (DMSO) in 400 ml of THF, 15 ml of hexamethylphosphoramide (HMPA) and 247 ml of $(CH_3)_3SOI$ were added and stirred. Then 11 4.4 g portions of 60% sodium hydride (NaH) were added every 15 minutes. The mixture was aged until all of gaseous $H_2$ had evaporated. 197 g of Cyclohexylidene-phenyl-acetonitrile was added dropwise for 1 hour. The mixture was aged for 3 hours and then quenched with 500 ml of cold water followed by 500 of toluene. A sample was taken. The gas chromatography test indicated that 92% of the starting material converted into 1-Phenyl-Spiro[2.5]Octane-1-Carbonitrile. The mixture was washed with 2 500 ml portions of cold water.

The product had fresh, floral, rosy, green, geranium like, ionone, soft, substantive tones.

The NMR spectrum of the 1-Phenyl-Spiro[2.5]Octane-1-Carbonitrile is as follows: 1.0 ppm (s, H); 1.1 ppm (m, H); 1.3 ppm (m, 1H); 1.4 ppm (s, 2H); 1.5 ppm (m, 2H); 1.7 ppm (m, 2H); 1.8 ppm (m, 2H); 1.9 ppm (d, H); 2.3 ppm (m, 1H); 2.7 ppm (d, 1H); 7.3 ppm (m, 5H).

EXAMPLE B

Preparation of
1-Phenyl-Spiro[2.5]heptane-1-Carbonitrile

To a dry 2 L multi-neck round bottom flask fitted with an air stirrer, nitrogen inlet condenser and an addition funnel 30 ml of Dimethyl Sufoxide (DMSO) in 60 ml of THF and 23 ml of $(CH_3)_3SOI$ were added and stirred. Then 4.4 g of 60% sodium hydride (NaH) was added. 19 g of Cyclopentylidene-phenyl-acetonitrile was added dropwise. The mixture was aged until all of gaseous $H_2$ had evaporated and heated to 50° C. The mixture was aged for 3 hours and then quenched with 50 ml of cold water followed by 50 of toluene. A sample was taken. The gas chromatography test indicated that 90% of the starting material converted into 1-Phenyl-Spiro[2.5]Heptane-1-Carbonitrile. The mixture was washed with 2 50 ml portions of cold water.

The product had fresh, floral, ionone, soft, substantive, and green tones.

The NMR spectrum of the 1-Phenyl-Spiro[2.5]Heptane-1-Carbonitrile is as follows: 1.2 ppm (m, H); 1.3 ppm (m, H); 1.5 ppm (m, 2H); 1.6 ppm (m, 1H); 1.7 ppm (m, H); 1.9 ppm (s, 3H); 2.2 ppm (s, H); 2.6 ppm (t, 1H); 2.8 ppm (t, H); 7.3 ppm (m, 2H); 7.4 ppm (m, 2H).

EXAMPLE C

Preparation of
1-Phenyl-2-Propyl-cyclopropanecarbonitrile

To a dry 2 L multi-neck round bottom flask fitted with an air stirrer, nitrogen inlet condenser and an addition funnel 150 ml of Dimethyl Sufoxide (DMSO) in 200 ml of THF, 15 ml of hexamethylphosphoramide (HMPA) and 140 ml of $(CH_3)_3SOI$ were added and stirred. Then 25 g of 60% sodium hydride (NaH) was added in small portions. The mixture was stirred over night at room temperature. The mixture was slowly brought up to 50° C. and maintained at this temperature until all of gaseous $H_2$ had evaporated. 91 g of 2-Phenyl-hex-2-enenitrile was added dropwise over 2 hours. The mixture was cooled to 30° C. and then quenched with 500 ml of cold water followed by 500 of toluene. A sample was taken. The gas chromatography test indicated that 93% of the starting material converted into 1-Phenyl-2-Propyl-cyclopropanecarbonitrile. The mixture was washed with 2 500 ml portions of cold water.

The product had fresh, floral, ionone, soft, substantive, citrus and green tones.

The NMR spectrum of the 1-Phenyl-2-Propyl-cyclopropanecarbonitrile is as follows: 1.0 ppm (m, 3H); 1.4 ppm (m, H); 1.5 ppm (s, H); 1.6-1.8 ppm (m, 5H); 7.2 ppm (m, 3H); 7.3 ppm (m, 2H).

Below is a prophetic example of using the compound of the present invention in a fragrance formulation.

EXAMPLE H

| Incorporation of 1-Phenyl-Spiro[2.5]Octane-1-Carbonitrile into a fragrance formulation | |
|---|---|
| Aldehyde AA Triplal | 5.00 |
| Allyl Heptoate | 4.00 |
| Benzyl Acetone | 13.00 |
| Cyclacet | 57.00 |
| Damascone Delta | 1.00 |
| Decanal | 2.00 |
| Dihydro Myrcenol | 125.00 |
| Eucalyptol | 5.00 |
| Galaxolide | 75.00 |
| Geraniol | 45.00 |
| Hexyl Cinnamic Aldehyde | 30.00 |
| Hydrocinnamonitrile, Alpha-Methyl-Alpha-Vinyl | 10.00 |
| Iso E Super | 75.00 |
| Linalool | 115.00 |

-continued

| Incorporation of 1-Phenyl-Spiro[2.5]Octane-1-Carbonitrile into a fragrance formulation | |
|---|---|
| Meth Ionone Iso Alpha | 60.00 |
| Methyl Anthranilate | 2.00 |
| Methyl Cedryl Ketone | 15.00 |
| Nerol | 30.00 |
| Orange Oil | 25.00 |
| 1-Phenyl-Spiro[2.5]Octane-1-Carbonitrile, | 40.00 |
| Phenyl Ethyl Alcohol | 100.00 |
| Rose Oxide | 1.00 |
| Terpineol | 30.00 |
| Terpinyl Acetate | 35.00 |
| Verdox | 100.00 |
| Total weight | 1000.00 |

What is claimed is:

1. A method of improving, enhancing or modifying a fragrance formulation through the addition of an olfactory acceptable amount of the compound of formula

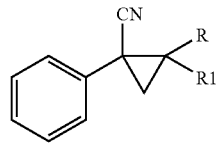

wherein R and R$^1$ independently represent a hydrogen or a straight, branched or cyclic hydrocarbon moiety consisting of less than 15 carbon atoms and containing single and/or double bonds.

2. The method of claim 1 wherein the fragrance is incorporated into a product selected from perfumes, colognes, toilet waters, cosmetic products, personal care products, fabric care products, cleaning products and air fresheners.

3. The method of claim 2 wherein the cleaning product is selected from the group consisting of detergents, dishwashing compositions, scrubbing compounds and window cleaners.

4. The method of claim 1, wherein the amount incorporated into a fragrance is from about 0.005 to about 10 weight percent.

5. The method of claim 1, wherein the amount incorporated into a fragrance is from about 0.5 to about 8 weight percent.

6. The method of claim 1, wherein the amount of incorporated into a fragrance is from about 1 to about 7 weight percent.

7. A compound

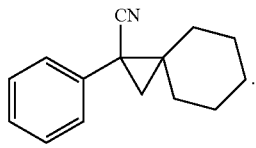

8. A compound

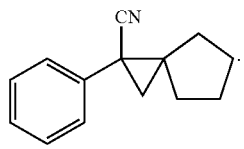

9. A compound

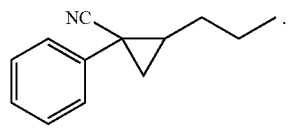

10. A compound of formula

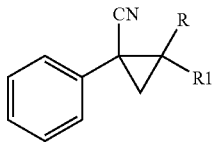

wherein R and R$^1$ taken together can form a cyclic hydrocarbon moiety consisting of less than 7 carbon atoms.

11. A method of improving, enhancing or modifying a fragrance formulation through the addition of an olfactory acceptable amount of the compound of claim 10.

12. The method of claim 11 wherein the fragrance is incorporated into a product selected from perfumes, colognes, toilet waters, cosmetic products, personal care products, fabric care products, cleaning products and air fresheners.

13. The method of claim 12 wherein the cleaning product is selected from the group consisting of detergents, dishwashing compositions, scrubbing compounds and window cleaners.

14. The method of claim 11, wherein the amount incorporated into a fragrance is from about 0.005 to about 10 weight percent.

15. The method of claim 11, wherein the amount incorporated into a fragrance is from about 0.5 to about 8 weight percent.

16. The method of claim 11, wherein the amount of incorporated into a fragrance is from about 1 to about 7 weight percent.

17. A fragrance formulation containing an olfactory effective amount of the compound of claim 10.

18. A fragrance product containing a compound of claim 10.

* * * * *